United States Patent [19]

Bowers

[11] Patent Number: 4,559,943
[45] Date of Patent: Dec. 24, 1985

[54] ELECTROSURGICAL GENERATOR

[75] Inventor: William J. Bowers, Aurora, Colo.

[73] Assignee: C. R. Bard, Inc., Murray Hill, N.J.

[21] Appl. No.: 547,964

[22] Filed: Nov. 2, 1983

Related U.S. Application Data

[62] Division of Ser. No. 299,204, Sep. 3, 1981, Pat. No. 4,438,766.

[51] Int. Cl.⁴ .............................................. A61B 17/39
[52] U.S. Cl. .............................. 128/303.14; 128/303.17
[58] Field of Search ..................... 128/303.13, 303.14, 128/303.17, 303.18

[56] References Cited

U.S. PATENT DOCUMENTS

| | | | |
|---|---|---|---|
| 3,885,569 | 5/1975 | Judson | 128/303.14 |
| 3,898,991 | 8/1975 | Ikuno et al. | 128/303.14 |
| 3,952,748 | 4/1976 | Kaliher et al. | 128/303.14 |
| 4,338,940 | 7/1982 | Ikuno | 128/303.14 |
| 4,429,694 | 2/1984 | McGreevy | 128/303.14 |

Primary Examiner—Lee S. Cohen
Attorney, Agent, or Firm—Wolf, Greenfield & Sacks

[57] ABSTRACT

A solid-state electrosurgical generator is disclosed which provides three separate output circuits that may be operated from a single common power source. One of the output circuits produces an output electrical waveform which is optimized for cutting and coagulation with monopolar electrodes. Another source provides a waveform which is optimized for cutting and coagulation with bipolar electrodes. The other electrosurgical source produces an output electrical waveform which is optimized for fulguration. The output circuits produce the optimized waveforms by appropriately processing electrical power provided by a D.C. power source. In order to do this, the output circuits may be connected to the power source by means of four semiconductor switches which may be arranged in either a bridge configuration for one output circuit or in a series arrangement for the other output circuit. The switches are, in turn, controlled by a timing circuit which provides different timing waveforms to the switches depending on their configuration.

11 Claims, 9 Drawing Figures

ELECTROSURGICAL GENERATOR

This application is a division of my application entitled, Electrosurgical Generator, filed Sept. 3, 1981 and assigned U.S. Ser. No. 299,204, now U.S. Pat. No. 4,438,766.

FIELD OF THE INVENTION

This invention relates to electrosurgery in general and in particular to electrosurgical generators which are capable of performing surgical operations by means of radio-frequency electrical currents.

BACKGROUND OF THE INVENTION

In addition to performing surgical operations on animal tissues by means of mechanical instruments such as scalpels or knives, surgery may also be performed by passing radio-frequency current through animal tissues. There are essentially four main surgical operations that can be performed depending on the voltage levels and the amount of power applied to the tissue. These operations are typically designated as dessication, fulgeration, cutting and cutting with hemostasis. Often, dessication is referred to as coagulation and sometimes dessication and fulguration are designated collectively as coagulation.

The radio-frequency current used in the performance of electrosurgical operations is typically generated by means of a radio-frequency generator connected to a power amplifier. The output of the power amplifier is in turn connected to the tissue mass by means of two electrodes. Surgical operations are performed by means of a "active" electrode which introduces the radio-frequency current into the tissue mass. Since, as mentioned above, electrosurgical effects are primarily dependent on the power and voltage applied, the active electrode typically has a small cross-section to concentrate the power and limit the surgical effects to a small, controlled area. A return path from the tissue mass to the generator for the radio-frequency current is provided by a "passive" or "patient" plate which has a large area to prevent electrosurgical effects from taking place at the current return location. Alternatively, a pair of active electrodes may be used in a "bipolar" mode in which the electrosurgical effects are confined to the sample of tissue between the two electrodes.

A dessication operation is performed by holding the active electrode in firm contact with the tissue. Radio-frequency current passes from the electrode directly into the tissue to produce heating of the tissue by electrical resistance heating. The heating effect destroys the tissue cells and produces an area of necrosis which spreads radially from the point of contact between the electrode and the tissue. Due to the nature of the cell destruction, the necrosis is usually deep. The eschar produced during the operation is usually light in color and soft. In order to produce optimal results in a dessication operation, an electrosurgical generator must be capable of providing several amperes (peak current) of radio-frequency current to moist tissue which has an impedance of approximately 100 ohms. Although the radio-frequency peak current density is high, the power delivered to the tissue is relatively low because of the low tissue impedance. In addition, the dessication waveform may be interrupted to produce an overall low duty cycle which helps to reduce cutting effects. Therefore, although the peak current values are high, the RMS value of the current is low. During a dessication operation the moisture in the tissue cells is driven off at a controlled rate and as the moisture content in the tissue decreases its impedance increases. Therefore, in order to keep the power applied to the tissue at a low value and prevent a cutting effects, as described below, it is necessary to limit the power output as the tissue impedance increases. Ideally, the power decrease should be proportional to the impedance.

As the impedance of the tissue increases, depending on the output characteristics of the electrosurgical generator, another surgical effect can be produced. Cutting occurs when sufficient power per unit time is delivered to the tissue to vaporize cell moisture. If the power applied is high enough a sufficient amount of steam is generated to form a layer of steam between the active electrode and the tissue. When the steam layer forms, a "plasma" consisting of highly ionized air and water molecules forms between the electrode and the tissue causing the tissue impedance, as seen by the generator, to rise to approximately 1000 ohms. If the electrosurgical generator can provide sufficient power to a 1000-ohm load and has sufficiently high output voltage, a radio-frequency electrical arc develops in the plasma. When this happens the current entering the tissue is limited to an area equal to the cross-sectional area of the arc where it contacts the tissue and thus the power density becomes extremely high at this point. As a result of the locally high power density the cell water volatizes into steam instantaneously and disrupts the tissue architecture—literally blowing the cells apart. New steam is thereby produced to maintain the steam layer between the electrode and the tissue. If the power density delivered to the tissue mass is sufficient, enough cells are destroyed to cause a cutting action to take place. A repetitive voltage waveform, such as a sinusoid, delivers a continuous succession of arcs and produces a cut with very little necrosis and hemostasis.

It is also possible to achieve a combination of the above effects by varying the electrical waveform applied to the tissue. In particular, a combination of cutting and dessication (called cutting with hemostasis) can be produced by periodically interrupting the continuous sinusoidal voltage normally used to produce an electrosurgical cut. If the interruption is of sufficient duration, the ionized particles in the plasma located between the electrode and the tissue diffuse away, causing the plasma to collapse. When this happens the electrode comes in contact with the tissue momentarily until a new plasma layer is formed. During the time that the electrode is in contact with the tissue it dessicates the tissue thereby sealing off small blood vessels and other bleeders in the vicinity of the electrode.

Another surgical effect called fulguration may be obtained by varying the voltage and power per unit time applied by the electrosurgical generator. Although fulguration is often confused with dessication, it is a distinctly different operation. In particular, fulguration is typically performed with a waveform which has a high peak voltage but a low duty cycle. If an active electrode with this type of waveform is brought close to a tissue mass and if the peak voltage is sufficient to produce a radio-frequency arc (at an impedance of 5000 ohms before electrical breakdown), fulguration occurs at the point where the arc contacts the tissue. Due to the low duty cycle of the fulgurating waveform, the power per unit time applied to the tissue is low enough so that cutting effects due to explosive volatization of cell moisture are minimized. In effect, the radio-frequency arc coagulates the tissue in the immediate vicinity of the active electrode thereby allowing the operating surgeon to seal off blood vessels in the vicinity of the electrode. The fulgurating electrode never touches the surface of the tissue and a hard, dark eschar is formed at the surface of the tissue mass in the fulgurated area. In contrast to dessication, fulguration is a surface process and the area of necrosis is confined to the surface. Therefore, fulguration can be used where the tissue mass is very thin and the deep necrosis produced by a dessication operation would damage underlying organs and accordingly, is a very useful operation.

In order to perform the above four surgical operations properly, a general-purpose electrosurgical generator must be capable of delivering significant amounts of radio-frequency power into a tissue impedance which varies over an order of magnitude (between approximately 100 ohms to approximately 1000 ohms). In addition, the generator must be capable of producing a sufficient peak voltage to initiate sparking in the fulguration and cutting modes. These requirements necessitate that the generator be capable of handling high internal radio-frequency voltages and currents.

In order to meet the internal generator demands the earliest prior art generators used oscillators and power amplifiers comprised of electron tube circuits. These prior art units had a disadvantage that they dissipated large amounts of heat internally. In order to handle the internal heat load the units were large and bulky and required ventilating fans which exhausted non-sterile air into the operating room environment.

To reduce the heat problem, subsequent prior art units used semiconductor components to generate the required radio-frequency power output. The semiconductor devices inherently dissipated less heat than the electron tube counterparts, but did not entirely eliminate the heat loading problem. When the semiconductor devices were used in a linear mode they still dissipated significant amounts of heat internally.

Other units utilized semiconductor switching circuits to produce rectangular waveforms instead of the sinusoidal waveforms used by the previous units. These rectangular waveforms could be generated more efficiently than sinusoidal waveforms but still did not entirely eliminate the heat problem. In particular, because the semiconductor devices in a practical general purpose generator are required to handle both high voltages and high currents, high power semiconductor switching devices were often used. These devices were able to handle the required voltages and currents, but had the disadvantage that their switching times were slow. A slow switching time results in high internal heat dissipation. Therefore, many prior art semiconductor devices still required large and bulky heat-sinks or ventilating fans. Although semiconductor components were available which had fast switching times and therefore low internal heat dissipation, these devices were not used in prior art general purpose electrosurgical generators because they were not inherently capable of handling the high voltages and high currents required. In addition, the use of a non-sinusoidal waveform produced significant amounts of radio-frequency noise due to the high order harmonics in the output signal.

Other prior art general purpose generators have attempted to overcome the internal heating problem by using several separate semiconductor generating circuits, each optimized for a particular electrosurgical operation. This prior art approach allows the semiconductor circuitry to be tailored to each output required for the associated electrosurgical operation. The tailoring reduces the current and voltage requirements placed on the semiconductors and thus semiconductors can be used which have faster switching times and thus less internal power dissipation. Unfortunately, the multiplicity of components necessary for this approach produces expensive and bulky units.

Still other units have solved the problem by optimizing the generator for one or two electrosurgical operations. These units are small and compact but typically produce poor results in surgical operations other than those for which they were designed.

SUMMARY OF THE INVENTION

The foregoing and other problems inherent in the prior art are solved by a general-purpose electrosurgical generator which utilizes high speed semiconductor switching circuitry to produce optimal voltage and current requirements for cutting, dessication, cutting with hemostasis and fulguration while maintaining low internal heat dissipation. Therefore, no large and bulky heat sinks or fans are required.

Specifically, the electrosurgical generator described in the illustrative embodiment herein utilizes a single output switching circuit and three output circuits. The switching circuit consists of four field effect transistor semiconductor switches driven by a common timing circuit. The interconnection of these semiconductor switches may be internally reconfigured under operator control so that, depending on the electrosurgical operation being performed, the switches may be connected in a bridge configuration or in a series configuration. In each configuration, the semiconductor switches are connected to handle the particular voltage and current requirements necessary to produce the optimal output power for the associated surgical operation. The timing waveforms produced by the timing circuitry which drive the switching circuit are also changed during each electrosurgical operation to produce optimal output waveforms.

More specifically, in configuring the unit to perform cutting and dessication operations, the four semiconductor switches are arranged in a bridge circuit. A filter circuit and output transformer are connected across the bridge configuration. The timing circuitry causes the semiconductor switches to operate as a full-wave bridge to provide rectangular pulses to the filter circuitry. These rectangular pulses can be generated efficiently, but, advantageously, the filter circuit converts the rectangular pulses into a sinusoidal waveform which efficiently drives the transformer and reduces radio-frequency noise which might otherwise be caused by high-order harmonics in the rectangular wave signal.

When the unit is configured to perform a fulguration operation, the four semiconductor switches are arranged in series to produce the high voltage necessary for satisfactory fulguration. The semiconductor switches are controlled by the timing circuit to act as a single switch in order to generate the waveforms to produce optimal fulguration results.

DESCRIPTION OF THE INVENTION

Figure 1:
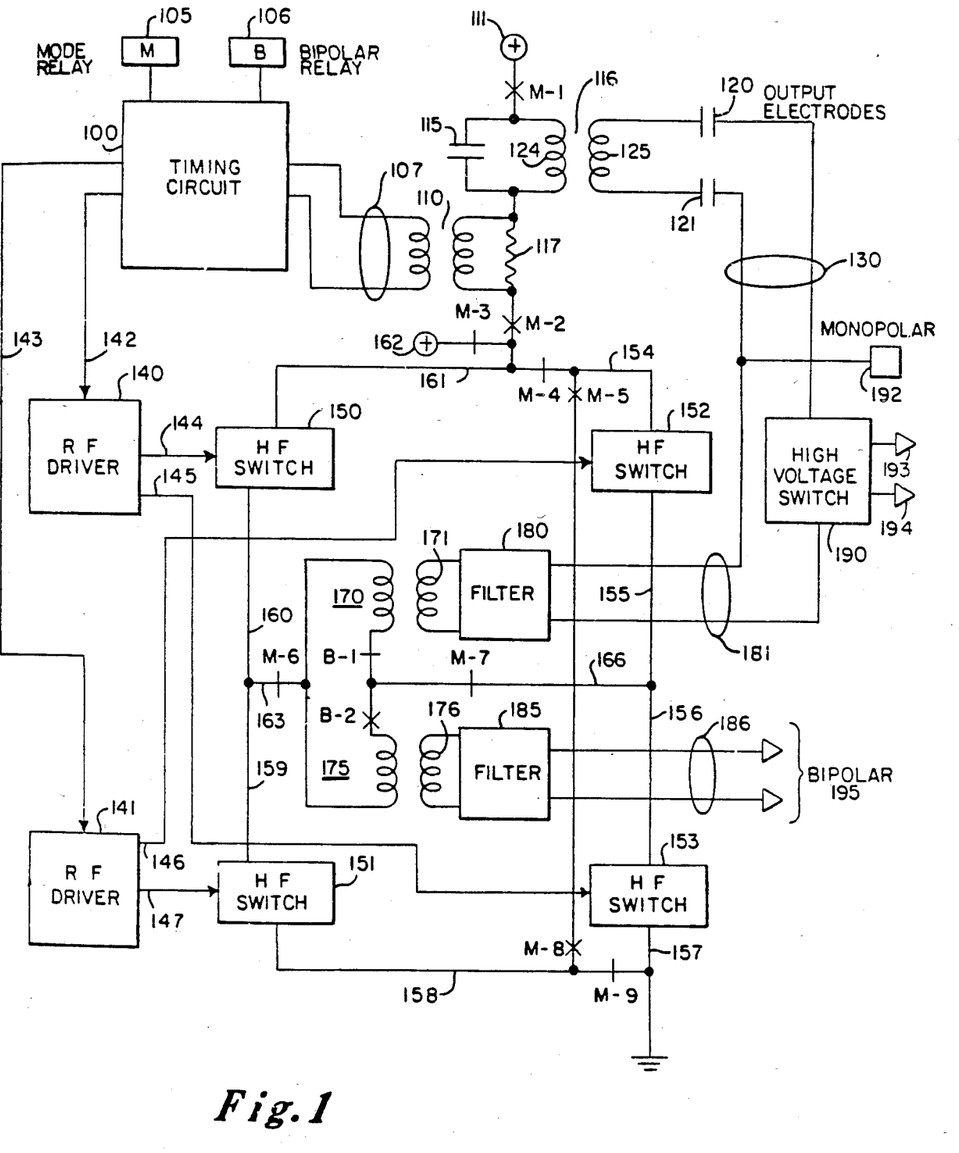
FIG. 1 shows a block diagram of the inventive electro surgical generator.

FIG. 1 of the drawing shows the schematic diagram of the output section of an illustrative electrosurgical generator. The generator has a separate output terminal set for use with monopolar electrodes (an electrode set which uses a single active electrode and a "patient" or return plate) and an output set for use with bipolar electrodes (where both electrodes are active). As will hereinafter be described more fully, each electrode set may be connected to output circuitry which produces optimal electrical waveforms for each electrosurgical operation. Specifically, the bipolar electrodes may be provided with waveforms which are optimized for dessication. The monopolar electrodes may be provided with waveforms that are optimized for dessication, cutting, cutting with hemostasis and fulguration.

According to the invention, the output circuitry is reconfigured automatically by internal generator circuitry according to the surgical operation selected by the surgeon.

Specifically, output waveforms produced by the generator are provided by three output transformers, one of which is selected according to the surgical operation desired—transformer 175 provides output to bipolar electrodes 195, via leads 186; transformer 170 provides cutting, cutting with hemostasis and coagulation waveforms to monopolar electrodes 192, 193 or 194 via leads 181; and transformer 116, in turn, provides a fulguration waveform, via leads 130, to monopolar electrodes 192, 193 or 194. Transformers 170 and 116 share a common return plate 192. However, the active side of leads 181 and 130 is connected to the appropriate electrode of electrodes 193 and 194 by high-voltage switch 190. High-voltage switch 190 may consist of a set of high-voltage relays which is controlled by either a hand or foot switch in accordance with well-known generator design.

Advantageously, in accordance with the invention, transformers 116, 170 and 175 are electrically driven by means of a single switching network which consists of four semiconductor switches 150–153. Switches 150–153 may be illustratively configured in a "bridge" configuration to provide full bipolar signals to drive transformers 170 and 175. In an alternate configuration, switches 150–153 may be connected in "series" to drive fulguration output transformer 116 as will be hereinafter fully described.

Switches 150–153 are, in turn, controlled by radio-frequency drivers 140 and 141. In order to drive the switches in a bridge configuration, driver 140 is connected to switches 150 and 153 via leads 144 and 145. Similarly, driver 141 is connected to switches 151 and 152, via leads 147 and 146, respectively. Drivers 140 and 141 are controlled to operate switches 150–153 in either of the two configurations by means of timing circuit 100 which operates drivers 140 and 141 by means of lead sets 142 and 143, respectively. Specifically, timing circuit 100 provides timing pulses via lead sets 142 and 143 which pulses, in turn, cause drivers 140 and 141 to close appropriate ones of switches 150–153 in order to provide carefully defined switching waveforms to the output transformers.

In addition to providing timing signals to the radio-frequency drivers, timing circuit 100 also controls mode relay 105 and bipolar relay 106. Mode relay 105 controls the electrical configuration of switches 150–153 by means of transfer contacts as will hereinafter be described. Bipolar relay 106 selects an appropriate one of transformers 170 and 175 to be activated by the bridge circuitry to produce an output.

Figure 9:
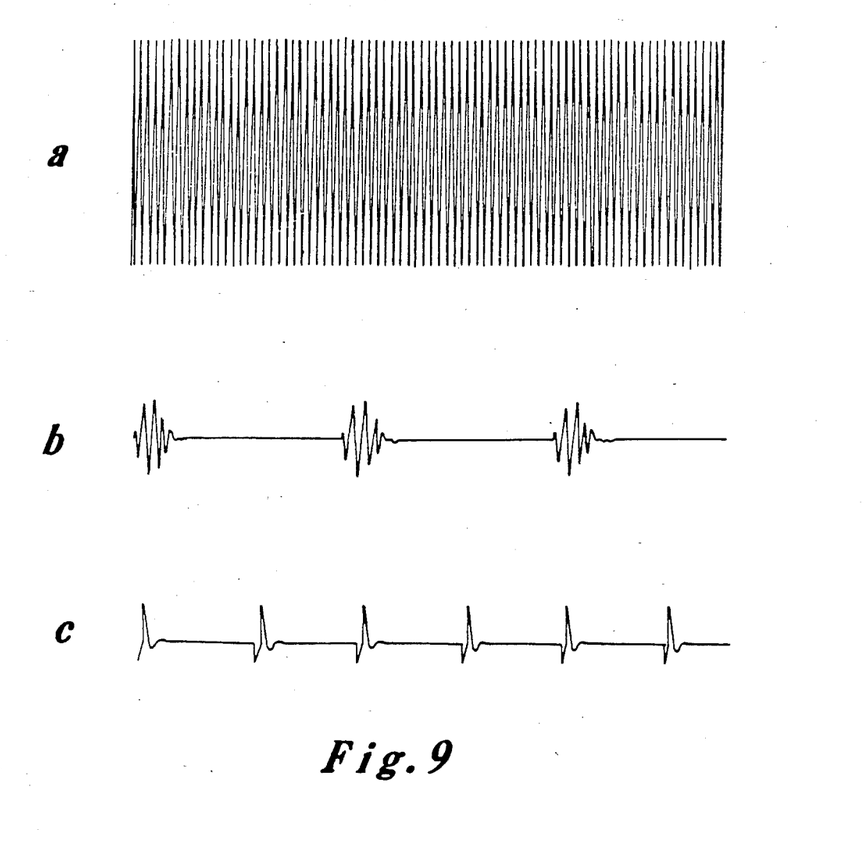
FIG. 9 shows output waveforms produced by the illustrative generator circuitry.

Each of the active modes for the three output transformers will now be described in detail. Assume, for purposes of illustration, that the operating surgeon has selected a cutting or dessication waveform to be produced on monopolar electrodes 192 and 193 or 194. Illustrative cutting waveforms and coagulation waveforms are shown in FIG. 9, lines A and B, respectively. In this case, the output waveform will be provided by transformer 170 under control of timing circuit 100. Specifically, under control of panel switches located on the generator front panel or remote foot or hand switches operated by the surgeon, timing circuit 100 releases both mode relay 105 and bipolar relay 106. In FIG. 1, these relays are shown with detached contacts. Normally-closed contacts are shown by lines drawn perpendicular to the associated electrical path. Alternatively, normally-open contacts are shown by crosses located on the associated electrical path. With this notation, released relay 105 opens its contacts M-1 and M-2, thereby disconnecting transformer 116 from power source 111 and the switching circuitry. Transformer 116 is thereby removed from operation. Similarly, released relay 106 opens its B-2 contact, thereby disconnecting transformer 175 from the circuitry.

Therefore, transformer 170 is the only transformer connected to the switching circuitry. Power is provided from source 162, via contact M-3, to semiconductor switch 150 via lead 161 and from source 162 to semiconductor switch 152 via contact M-4 and lead 154. Source 162 may illustratively be a regulated D.C. supply which produces a D.C. voltage of between 0 and 200 volts D.C. Any regulated supply may be used. For example, a supply which is suitable for use with the illustrative embodiment is a Sorensen Model DCR 600-3B. The power supply may be controlled from controls on the control panel of the electrosurgical generator or may be controlled by a feedback network to provide constant power under varying load conditions. A feedback network suitable for use with the illustrative embodiment is disclosed in U.S. Pat. No. 3,601,126 issued on Aug. 24, 1971 to J. R. Estes.

Semiconductor switches 150 and 152 are, in turn, connected directly to switches 151 and 153 by means of leads 160 and 159 and leads 155 and 156, respectively. Switches 151 and 153 are connected to ground by means of leads 158, contact M-9 and lead 157, respectively. The switches and leads form an electrical bridge network with one switch located in each arm of the bridge. The primary of output transformer 170 is connected across the center of the bridge by means of leads 165, contact M-6, lead 166, contact M-7 and contact B1. As will be hereinafter fully described, timing circuit 100 operates drivers 140 and 141 to in turn operate the semiconductor switches so that diagonally-opposite switches are simultaneously enabled. The switches then operate as a full-wave bridge which provides alternating signals to transformer 170. Specifically, timing circuit 100 controls driver 140 by means of leads 142 to first close switches 150 and 153. Current then flows from source 162 to ground via the following path: contact M-3, lead 161, switch 150, lead 160, lead 165, contact M-6, primary of transformer 170, contact B-1, contact M-7, lead 166, lead 156, switch 153, lead 157 to ground. After a predetermined time interval, timing circuit 100 causes driver 140 to open switches 150 and 153 interrupting the current flow. Subsequently, driver 141 is controlled to close switches 151 and 152. Current then flows (in the opposite direction) in the primary of transformer 170 via the following path: source 162, contact M-3, contact M-4, lead 154, switch 152, lead 155, lead 166, contact M-7, contact B-1, primary of transformer 170, contact M-6, lead 165, lead 159, switch 151, lead 158, contact M-9 to ground.

In this manner, timing circuit 100 alternately controls switches 150, 153 and switches 151, 152 to provide alternating signals to the primary of transformer 170. The above-described bridge arrangement of switches 150–153 has several advantages. Advantageously, although a voltage equal to twice the full supply voltage from supply 162 appears across the primary of transformer 170 only the supply voltage appears across any one switch. This feature allows very fast FET switches to be used as the semiconductor switches. Thus, the efficiency of the switching circuits is improved but high-voltage breakdown problems which are typically encountered with the use of such switches are avoided. In addition, since full-wave operation is used there is no center-tap on the primary of transformer 170. This configuration avoids residual flux coupling on the opposite section of the center-tapped transformer which is a major cause of radio-frequency noise that is undesirable in an operating room environment.

Figure 7:
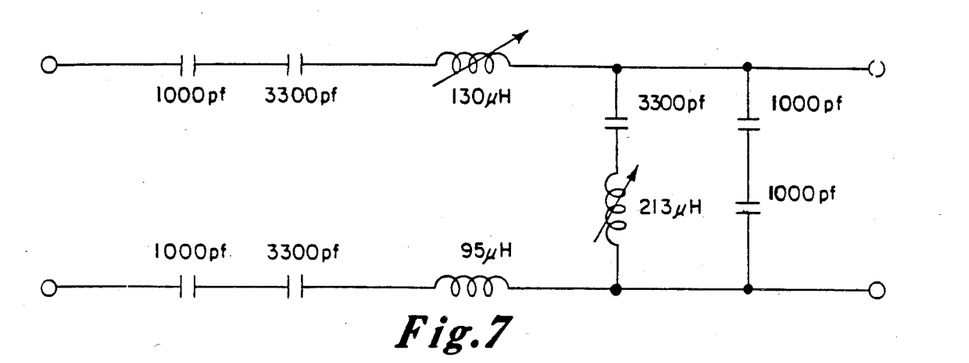
FIG. 7 shows a circuit diagram of the output filter for use with the monopolar output of the illustrative embodiment.

Also, advantageously, according to the invention, the signals that are provided to the primary of transformer 170 are square wave pulses which are efficiently generated by switches 150–153. These pulses are in turn coupled to secondary 171 of transformer 170 and are provided to filter circuit 180. Filter circuit 180 is illustratively a bandpass filter circuit as shown in FIG. 7.

Filter circuit 180 provides two functions in accordance with the invention. First, it filters out the high-frequency components of the switching waveform coupled to the secondary 171 of transformer 170. The output of filter circuit 180 provided on leads 181 is therefore approximately a sine wave with a fundamental frequency of 500 kilohertz. The removal of the high-frequency components of the signal by filter circuit 180 prevents the generation of radio-frequency noise and allows easier control and elimination of radio-frequency leakage paths from the active electrode to ground or from the patient to ground. However, the rectangular waveform provided to filter circuit 180 may be efficiently generated by means of transistor switching circuitry operating in a "class D" mode. When operating in a class D mode the semiconductor bridge switching circuitry dissipates less power and therefore no fan is needed to cool the internal circuitry of the generator. Since a fan is one source of contamination in the operating room environment, its elimination results in a unit which is safer for the patient's health.

Secondly, in accordance with the invention, when the output circuitry is operating in the coagulation mode with an interrupted waveform, filter circuit 180 produces a voltage doubling effect. More particularly, the peak voltage of the output waveform generated on output leads 181 is increased to twice the peak voltage of the rectangular waveform provided to filter circuit 180 from the secondary winding 171 of transformer 170. The increased output voltage in the coagultion mode helps to increase the electrical arc length resulting in an optimum output waveform.

As previously described, one of leads 181 is connected to patient return plate 192 and the other lead is connected, via high-voltage switch 190, to active output electrode 194 or 193.

Figure 8:
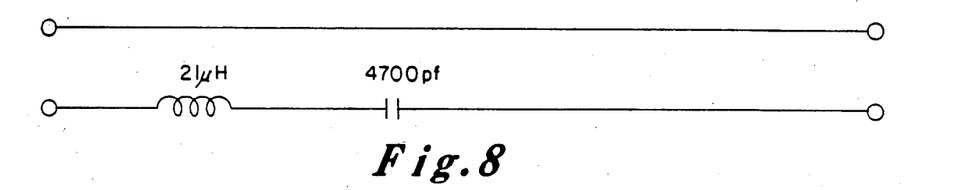
FIG. 8 shows a circuit diagram of the output filter for use with the bipolar output of the illustrative embodiment.

Assume now for the purposes of illustration, that the operating surgeon desires to use bipolar electrode 186. In this case, in response to actuation of panel or remote switches (not shown) by the operating surgeon, timing circuit 100 operates bipolar relay 106. Operated relay 106 opens its contact B-1 and closes contact B-2. Transformer 170 is thereby disconnected from the bridge circuitry and transformer 175 is connected. Operation of the circuit then proceeds in the manner exactly analogous to that previously described. Bipolar pulses provided to the primary of transformer 175 are coupled to secondary 176 and applied to filter circuit 185 which is shown in more detail in FIG. 8. The filtered output is provided to bipolar electrodes 195.

Assume now that by suitable switches, the operating surgeon choses a fulguration output to be produced on monopolar electrodes 192 and 193 or 194. An illustrative fulguration output is shown in line C of FIG. 9. In this case, timing circuit 100 is controlled by panel or remote switches (not shown) to actuate mode relay 105 and release bipolar relay 106. Operated relay 105 opens contacts M-6 and M-7, thereby isolating transformers 170 and 175 from the switching circuitry. Operated relay 105 also opens contact M-3, disconnecting power supply 162 from the switching circuitry, and closes contacts M-1 and M-2 thereby connecting transformer 116 in series with power supply 111 and switches 150–153. Finally, operated relay 105 closes contacts M-5 and M-8 and opens contacts M-4 and M-9, thereby connecting switches 150–153 in series with transformer 116 and the power supply ground.

Also, as will hereinafter be explained in detail, timing circuit 100 is conditioned in response to the operator of the panel or remote switches to control drivers 140 and 141 to close and open switches 150–153 simultaneously, thus effectively repetitively connecting the primary of transformer 116 between power supply 111 and ground. In particular, primary 124 of transformer 116 is connected in parallel with capacitor 115 and forms a high-frequency resonant "tank" circuit. When the lower end of primary winding 124 is connected to ground, current flows from power supply 111 through contact M-1 and primary 124 of the transformer. Subsequently, when timing circuit 100 causes drivers 140 and 141 to, in turn, open switches 150–153, the tank circuit "rings down" to produce a damped sinusoidal output (as show in line C of FIG. 9). Since timing circuit 100 periodically closes and opens switches 150–153, a periodic damped sinusoidal waveform is produced. This periodic waveform is coupled to the secondary 125 of transformer 116 and is provided (through capacitors 120 and 121 and leads 130) to the monopolar electrodes consisting of patient plate 192 and output electrode 193 or 194.

The components of the high-frequency tank circuit are chosen to produce a waveform which is optimized for a surgical fulguration operation. The particular details of the fulguration output circuitry do not form a portion of the invention described herein and will not be described in further detail. A detailed explanation of fulguration circuitry which may be used with the illustrative embodiment disclosed herein is given in a copending patent application entitled "Electrosurgical Generator" filed July 6, 1981 by Francis T. McGreevy, designated Ser. No. 281,005 and assigned to the same assignee as the present invention.

Specifically, in order to excite the high-frequency tank circuitry, timing circuit 100 repetitively opens and closes switches 150–153 by means of driver circuits 140 and 141. Current then flows from source 111 through the following pathway: contact M-1, primary 124 of transformer 116, resistor 117, contact M-2, lead 161, switch 150, leads 160 and 159, switch 151, lead 158, contact M-8, contact M-5, lead 154, switch 152, leads 155 and 156, switch 153, lead 157 to power supply ground. When switches 150–153 are opened, a relatively high voltage is produced by the "back E.M.F." induced in primary winding 124 of transformer 116. However, since switches 150–153 are connected in a series configuration, the high voltage is divided across all four switches, thus preventing a secondary breakdown of any one of the switches even though FET switches are used.

In order to further protect the FET switches, a current sensing circuit consisting of resistor 117 and transformer 110 has been provided. Current flowing through the circuit develops a voltage across resistor 117 which voltage is, in turn, coupled, via transformer 110 and leads 107, to timing circuit 100. As will be hereinafter described, an increase in current flowing through resistor 117 above a predetermined threshold causes the "on" time of switches 150–153 to be reduced, thereby reducing the average current flowing through the switches and preventing any damage caused by overcurrent.

Figure 2:
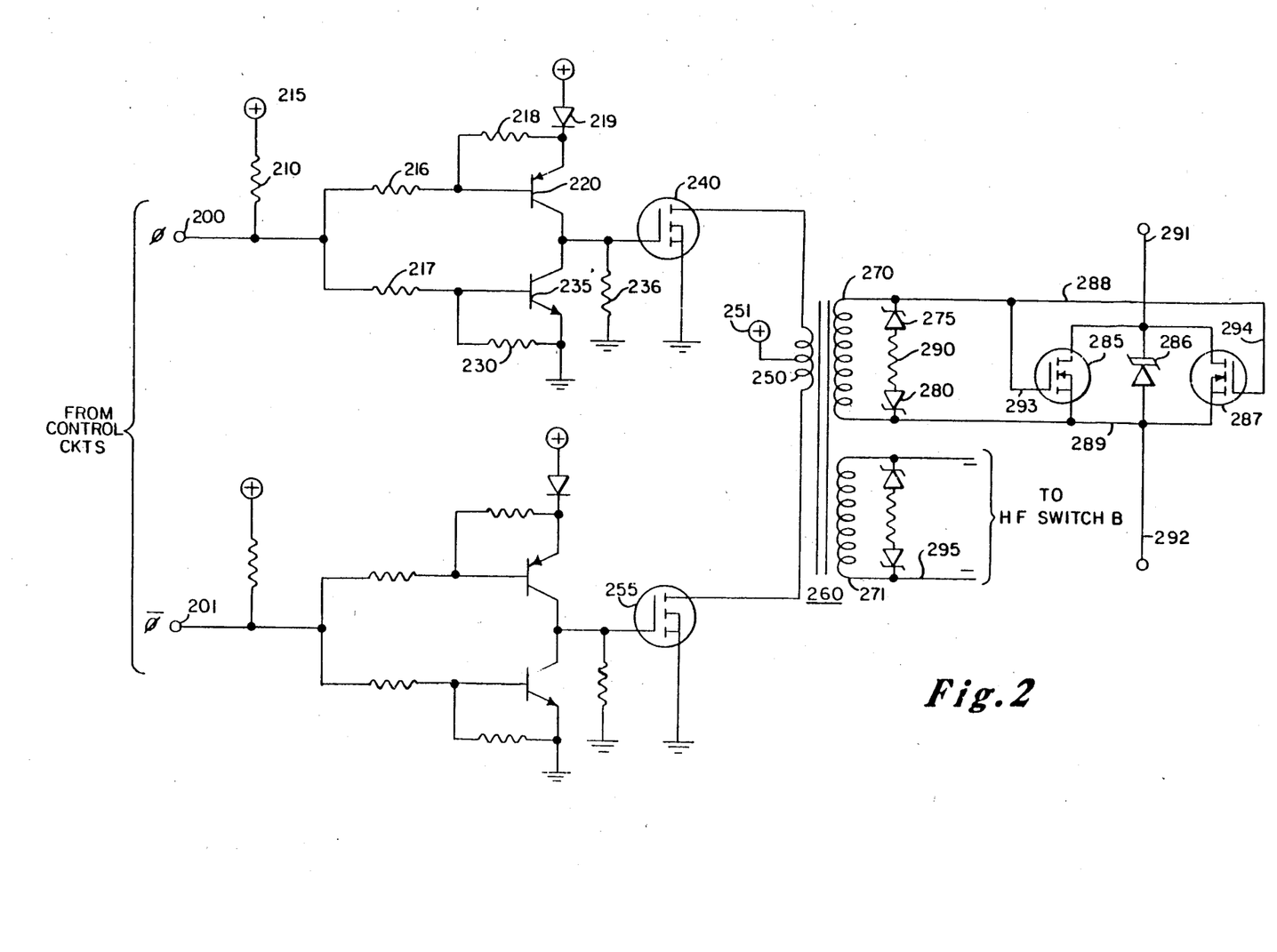
FIG. 2 discloses the detailed circuitry of the radio-frequency driver circuits and semiconductor switches.

The detailed circuitry of the semiconductor switches and driver circuits 140 and 141 is shown in FIG. 2. Each of driver circuits 140 and 141 contains identical circuitry so, for clarity of description only one driver circuit will be shown in detail. Likewise, each semiconductor switch 150–153 is identical and therefore only one switch will be described in detail. Referring to FIG. 2, the circuity of the driver circuits is shown in detail. The driver circuits are controlled by the signals $\phi$ and $\overline{\phi}$ provided from the control circuit via terminals 200 and 201 shown at the left side of FIG. 2. The driver unit itself consists of two driver switch units which are identical. Since the switch units are identical only one will be described in detail.

Each driver switch unit of driver 140 is connected to one end of center-tapped transformer 260. The secondary of transformer 260 drives the semiconductor switches. In the quiescent or "off" state, input 200 of the upper unit is normally held at a "high" voltage by logic circuitry in the timing circuitry. In addition, resistor 210 which is connected to positive voltage source 215 helps to hold input 200 "high". The positive voltage on terminal 200 is applied via the resistive divider, consisting of resistors 217 and 230, to the base of transistor 235, turning it "on". In its "on" state, transistor 235 places a low signal (near ground) on its collector. The gate electrode of FET switch 240, which is connected to the collector of transistor 235, is thus held at ground and FET 240 is therefore held "off". In addition, the high signal appearing on terminal 200 is applied via the resistive divider, consisting of resistors 216 and 218, to the base of transistor 220 holding it in its "off" state.

The driver unit becomes active when the control circuitry places a negative-going pulse on terminal 200. The negative-going pulse is applied, via the resistive divider consisting of resistors 217 and 230, to the base of transistor 235, turning it "off". In addition, the negative-going pulse is applied via the resistive divider, consisting of resistors 216 and 218, to the base of transistor 220, turning it "on". Current thus flows through diode 219 and transistor 220 and resistor 236 to ground, raising the potential on the gate lead of FET switch 240. In response thereto, FET switch 240 turns "on" and current flows from positive voltage source 251 through one half of the primary windings 250 of transformer 260 through FET switch 240 to ground. Transformer 260, in turn, controls the semiconductor switches by means of two secondary windings 270 and 271 (in the diagram, for clarity, only winding 270 is shown connected to a semiconductor switch. Winding 271 is connected in an analogous manner to another switch). The output of winding 270 is connected to the gate and source electrodes of the semiconductor FET switches. In addition, a pair of Zener diodes 275, 280 (having a breakdown voltage rating of approximately 12 volts) in series with resistor 290 are connected across winding 270. These three components prevent an accidental high-voltage spike occurring across secondary 270 from damaging the semiconductor switch transistors.

At the end of the "on" time interval, the voltage on terminal 200 provided by the timing circuit again returns to its quiescent "high" state, transistor 235 turns "on" and transistor 220 turns "off", thereby allowing resistor 236 to return the potential on the gate electrode of FET 240 to ground. Responsive thereto, FET 240 ceases conducting and current ceases flowing from source 251 through the primary winding 250 of transformer 260.

However, in order to insure quick turnoff of the semiconductor switches, the current in the primary winding 250 of transformer 260 is effectively "reversed" to "dump" the flux in the transformer windings insuring that the voltage in the secondary falls quickly to zero. In particular, as hereinafter described, a short time after terminal 200 returns to its quiescent "high" state, the control circuitry places a short negative-going pulse of approximately 200 nanoseconds in duration on terminal 201. In a manner analogously described to the upper driver switch circuit, the lower driver switch circuit in the radio-frequency driver turns "on" FET 255, causing current to flow from source 251 through the primary winding 250 of transformer 260. This current will be flowing in a direction opposite to the immediately previous current flow. The magnetic flux resulting in the transformer core is in a direction opposite to that produced by the negative-going pulse on terminal 200. Any residual flux in the core will thus be "cancelled" insuring quick turnoff of the semiconductor switches.

Figure 3:
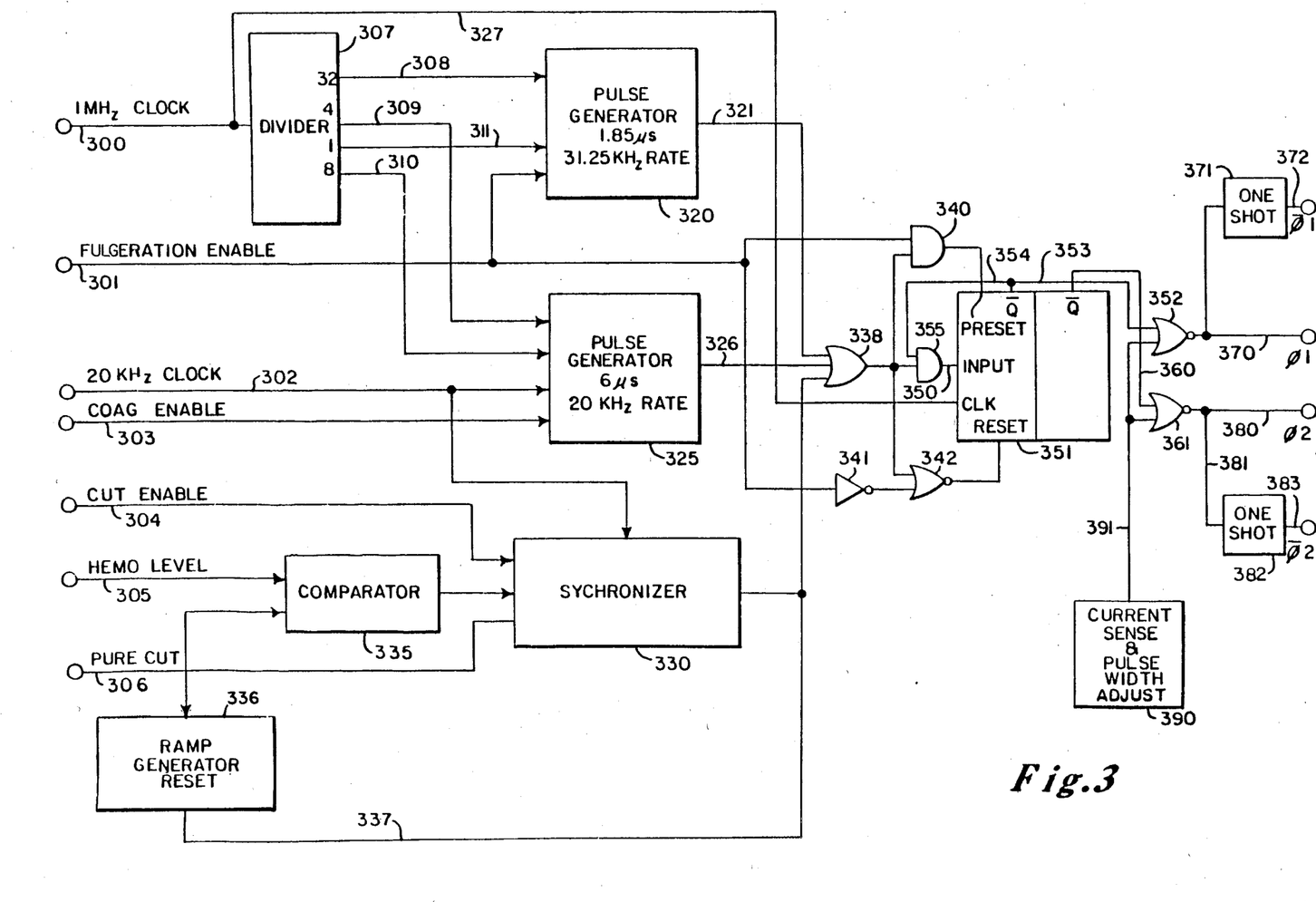
FIG. 3 is a block schematic diagram of a timing circuit suitable for use with the illustrative embodiment.

FIG. 3 of the drawing shows a simplified block diagram of the timing circuit which controls the radio-frequency drivers and, in turn, the semiconductor switches to operate the bridge switching network.

The timing circuit is provided with a number of inputs which control and synchronize its operation. In particular, two clock signals are provided on leads 300 and 302. The clock signal on lead 300 is a one megahertz clock signal and that on 302 is a twenty kilohertz clock signal. These clock signals may be provided by well-known clock generation circuitry (not shown). In addition to the clock signals, the timing circuit also receives several mode-enabling signals on leads 301 and 303–305. The mode signals are generated by the switches which may be located on the front panel of the electrosurgical generator or the signals may be generated by logic circuitry (not shown) which is, in turn, controlled by remote foot or hand switches in accordance with well-known surgical practice. Lead 301 is provided with a logical signal that is "high" when a fulgurating output waveform is desired by the operating surgeon. Similarly, lead 303 is provided with a "high" signal when a waveform optimized for dessication (coagulation) is desired. The signal on lead 304 is "high" when an output waveform optimized for surgical cutting is desired. The signal on lead 306 selects whether the output waveform will be optimized for pure cutting or for cutting with hemostasis (the signal is "high" in the latter case and "low" in the former). If a waveform optimized for cutting with hemostasis is selected, a D.C. level is provided from a potentiometer connected to a dial on the front panel of the generator (not shown) on lead 305 which, as will be hereinafter described, selects the duty cycle ("on"-time) of the cutting waveform to produce the desired cutting with hemostasis effect. The input signals on leads 301 and 303 through 306 may be provided by logic circuits (not shown) which insure that only one output mode is selected at any given time. Construction of such logic circuits is straightforward and would be obvious to one skilled in the art.

The timing circuit in FIG. 3 produces two sets of output signals shown at the righthand side of the Figure and designated as $\phi1$, $\overline{\phi1}$, and $\overline{\phi2}$, $\phi2$. Each of the $\phi1$ and $\phi2$ outputs are provided to a respective input of one of the driver circuits shown in FIG. 2 to, in turn, control the semiconductor switches.

As will be hereinafter described, in accordance with the invention, the timing circuitry is reconfigurable under control of the mode-enabling signals so that the two radio-frequency driver circuits may operate either simultaneously or alternately in order to provide optimal output waveforms for each selected surgical operation.

Specifically, the one megahertz clock signal provided on input lead 300 is applied to divider 307. Divider 307 is a well-known digital device which receives a clock signal at its input and provides a number of outputs each of which is a squarewave signal having frequency which is a fixed sub-multiple of the input clock signal. For example, divider 307 receives the one megahertz clock signal at its input and provides four outputs which are produced at frequencies equal to $\frac{1}{2}$, $\frac{1}{4}$, $\frac{1}{8}$ and 1/32 of the input frequency and a signal at the input frequency. Thus, an output signal having a frequency of 31.25 kilohertz appears on lead 308. A signal having a frequency of 250 kilohertz appears on lead 309, a signal having a frequency of 125 kilohertz appears on lead 310 and a signal with a frequency of 500 kilohertz appears on lead 311. The 31.25 kilohertz and 500 kilohertz signals on leads 308 and 311 are provided to pulse generator 320 and the 250 kilohertz and 125 kilohertz signals on leads 309 and 310 are provided to pulse generator 325. Pulse generator 320 also receives a signal from the FULGURATION ENABLE lead 301 and pulse generator 325 receives an enable signal from the COAG ENABLE lead 303 and an additional clock signal from 20 KHZ CLOCK lead 302. As will be hereinafter described, in response to its three input signals, pulse generator 320 provides an output on lead 321 which consists of a train of pulses, each having a duration of 1.85 microseconds and a repetition rate of 31.25 kilohertz. Similarly, in response to its four inputs, pulse generator 325 produces a pulse train having pulses of six microseconds duration and a repetition rate of 20 kilohertz. The output of generator 320 on lead 321 and the output of generator 325 on lead 326 is provided to ORgate 338. ORgate 338 is an enabling gate which provides a "high" signal at its output 350 to the input of shift register 351 when a "high" signal is received at any of its three inputs. This "high" signal enables the shift register to produce output signals as will be hereinafter described. Shift register 351 is utilized as a free-running oscillator and synchronization circuit depending on the operating mode of the circuit. The outputs of register 351 on leads 353 and 360 are provided (after some preliminary processing) to the radio-frequency driver circuits which, in turn, drive the semiconductor switches to produce the generator output waveforms.

Advantageously, register 351 may be operated in one of two modes depending on the configuration of the bridge switching circuitry and the output waveform desired by the operating surgeon. In particular, the $\overline{Q}$ output of the first stage of register 351 is connected via lead 354 to one input of ANDgate 355. The output of gate 355 is connected to the input of the shift register. Since the $\overline{Q}$ output is an inverting output, the first stage of register 351 acts as a "toggle" flip/flop when gate 355 is enabled. That is, it changes state or oscillates on the reception of the positive-going edge of each clock pulse (since the shift register is driven by the one magehertz clock signal, the outputs change state at a 500 kilohertz rate). In accordance with the well-known operation of shift registers, the output $\overline{Q}$ of the first stage of register 351 is transferred on each clock pulse to the second stage. Thus the output $\overline{Q}$ of the second stage is equivalent to the output $\overline{Q}$ of the first stage of register 351, delayed by one clock pulse. The two stages of register 351 therefore act as out-of-phase clock sources when gate 355 is enabled and are used to drive opposite sides of the semiconductor switch bridge. This operation occurs during the cutting, cutting with hemostasis, dessication, bipolar cut and bipolar Coag modes of operation of the electrosurgical generator.

However, during the operation of the circuitry in the fulguration mode, a "high" signal is provided on the FULGURATION ENABLE lead 301 and gates 340 and 342 (the "high" signal on lead 301 is inverted by inverter 341 and applied as a "low" signal to enable NORgate 342) are enabled. Therefore, the "high" signal provided by ORgate 338 (in response to the pulses produced on lead 321 by pulse generator 320) is applied through gate 340 to the preset input of shift register 351 and through gate 342, via invertor 341, as a "low" signal to the reset input of shift register 351. In accordance with well-known operation of shift registers, the preset and reset inputs of shift register 351 override any signals on the input and cause all stages to be simultaneously preset or reset, respectively, (cause the outputs Q to go "low" or "high", respectively). Therefore, during the fulguration mode, in response to pulses provided by ORgate 338, the stages of shift register 351 are set and reset in synchronism. The outputs of shift register 351, in turn, control the semiconductor switching bridge and, as previously described, all semiconductor switches are thereby turned "on" and "off" simultaneously to produce the optimal output waveform for fulguration.

The outputs of shift register 351 on leads 353 and 360 are provided to one input of NORgates 352 and 361, respectively. The other inputs of NORgates 352 and 361 receive a signal on lead 391 from current sense and pulse width adjustment circuit 390. As will be hereinafter described, current sense and pulse width adjustment circuit 390 reduces the pulse width of the output pulses provided via gates 352 and 361 to the radio-frequency drivers in the event that the current flowing through the semiconductor switch transistors exceeds a predetermined value. In addition, circuit 390 adjusts the width of the output pulses so that there is no overlap between sucessive pulses. An overlap could cause both arms of the semiconductor bridge to be simultaneously "on", a condition which could damage the circuitry. In this way the semiconductor switch transistors are protected against an overload condition which would damage or destroy them.

More specifically, the output of gate 352 is provided, via lead 370, to the $\phi 1$ output terminal and used as previously described to drive one pair of semiconductor switches. In addition, the output of gate 352 is also provided to one-shot multivibrator 371 which is used to produce a short-duration, slightly delayed pulse on the $\overline{\phi 1}$ output 372 which, as previously described, is used by the radio-frequency drivers to ensure complete turnoff of the semiconductor switches. Similarly, the output of NORgate 361 is provided, via lead 380, to the output terminal $\phi 2$ and used to drive the other pair of semiconductor switches. The output of gate 361 is also provided, via lead 381, to one-shot multivibrator 382 which also produces a slightly delayed, short-duration pulse on output lead 383 to ensure proper turnoff of the associated semiconductor switches.

Assume, now, for purposes of illustration, that the timing circuitry is configured to produce an output optimized for coagulation or dessication. In this case, the FULGURATION ENABLE lead 301 has a "low" signal thereon. The COAG ENABLE lead 303 has a "high" signal thereon and the CUT ENABLE lead 304 has a "low" signal thereon. Pulse generator 325 receives a 250 kilohertz signal from divider 307, via lead 309, and a 125 kilohertz clock signal, via lead 310, from divider 307. In addition, pulse generator 325 receives a 20 kilohertz clock signal from lead 302 and the "high" signal on COAG ENABLE lead 303. In response to these signals, generator 325 produces six microsecond duration pulses at a 20 kilohertz repetition rate and these pulses are provided, via lead 326, to ORgate 338. As previously described, since the signal on FULGURATION ENABLE lead 301 is "low", gates 340 and 342 are disabled. Thus, shift register 351 operates as two out-of-phase clocks which drive opposite halves of the semiconductor switch bridge to produce a coagulation waveform. Since the signal on lead 326 is "high" for only six microseconds and shift register 351 operates at a 500 kilohertz rate, three pulses are produced by shift register 351 during each pulse produced by pulse generator 325.

Assume now that the timing circuitry is configured to produce an output signal optimized for electrosurgical cutting. In this case, CUT ENABLE lead 304 has a "high" signal thereon and COAG ENABLE lead 303 and FULGURATION ENABLE lead 301 have "low" signals thereon. In response to the low signals on leads 301 and 303, pulse generators 320 and 325 are disabled. The cut mode of operation has two distinct types of operation: pure cutting and cutting with hemostasis. In a purse cut operation a "high" signal also appears on the PURE CUT lead 306. Responsive to these signals, synchronizer 330 provides a constant "high" signal to ORgate 338. The "high" signal enables shift register 351 to cycle continuously under control of the one megahertz clock provided via lead 327. Free running shift register 351 produces a continuous signal which drives opposite halves of the semiconductor switch bridge to produce, after filtering by the output circuitry, a sine wave output suitable for electrosurgical cutting.

The circuitry is configured to produce an optimal output waveform for cutting with hemostasis when a "high" signal appears on CUT ENABLE lead 304 and a "low" signal appears on PURE CUT lead 306. Under these conditions, synchronizer 330 produces a "high" signal on its output to enable ORgate 338 under control of comparator 335. In particular, a D.C. voltage level representative of the percentage of time during which output power is to be produced by the generator is provided on HEMO LEVEL lead 305 to comparator 335. This D.C. level is compared to a voltage generated by ramp generator 336. When the output generated by ramp generator 336 is below that of the HEMO LEVEL lead 305, comparator 335 produces a "low" output enabling synchronizer 330 to produce a "high" output to, in turn, enable ORgate 338. As previously described, when ORgate 338 is enabled, shift register 351 runs continuously to produce a sine wave at the generator output. However, when the signal produced by ramp generator 336 equals the D.C. level on HEMO LEVEL lead 305, comparator 335 produces a "high" signal which disables synchronizer 330, in turn, disabling ORgate 338 and stopping shift register 351. In addition, the output of synchronizer 330 is applied, via lead 337, to reset ramp generator 336. Therefore, by varying the D.C. voltage level on HEMO LEVEL lead 305, the duration of the cutting signal can be varied.

Figure 4:
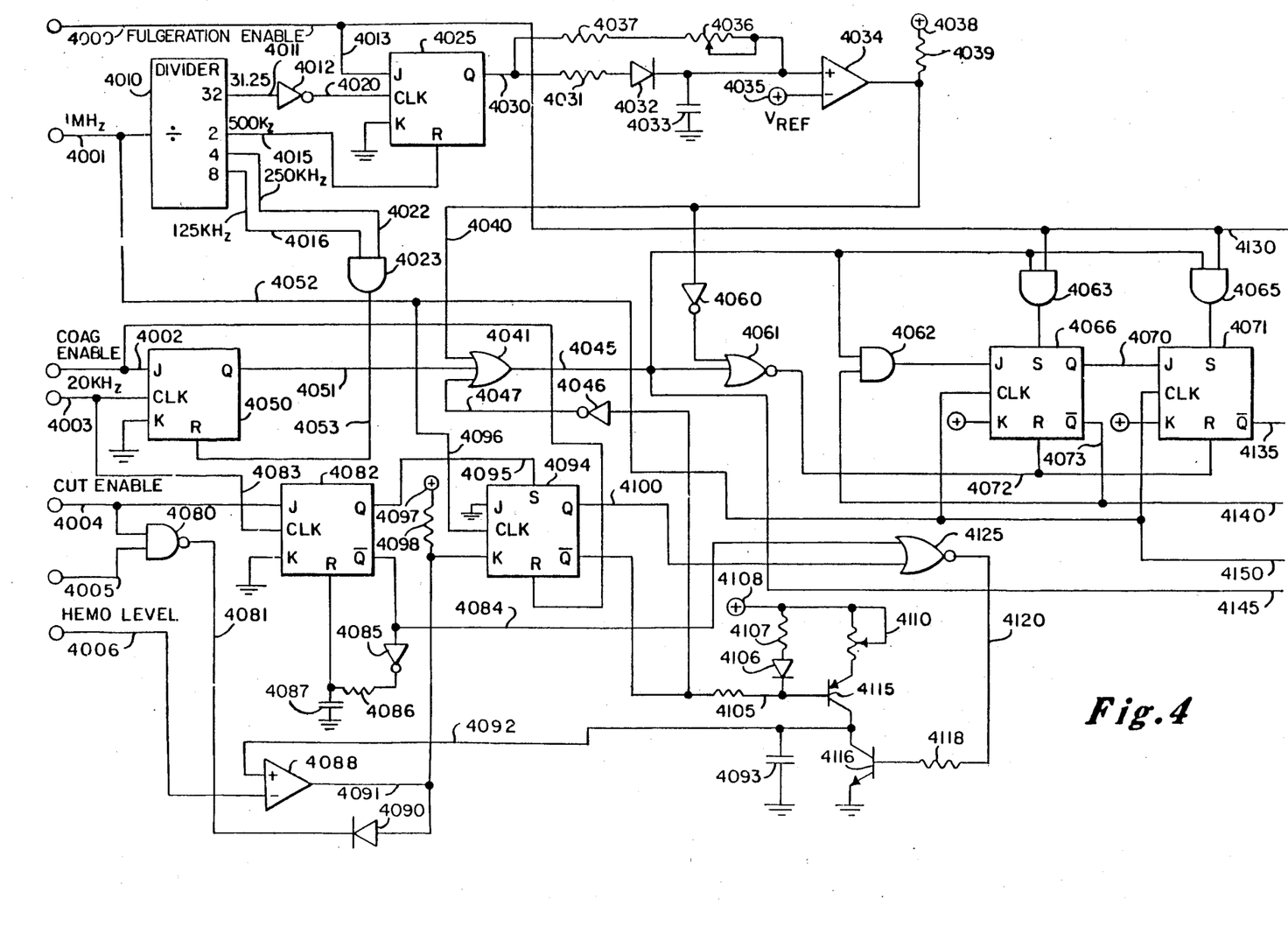
FIGS. 4 and 5 are detailed schematic diagrams of the circuitry shown in block form in FIG. 3.
Figure 5:
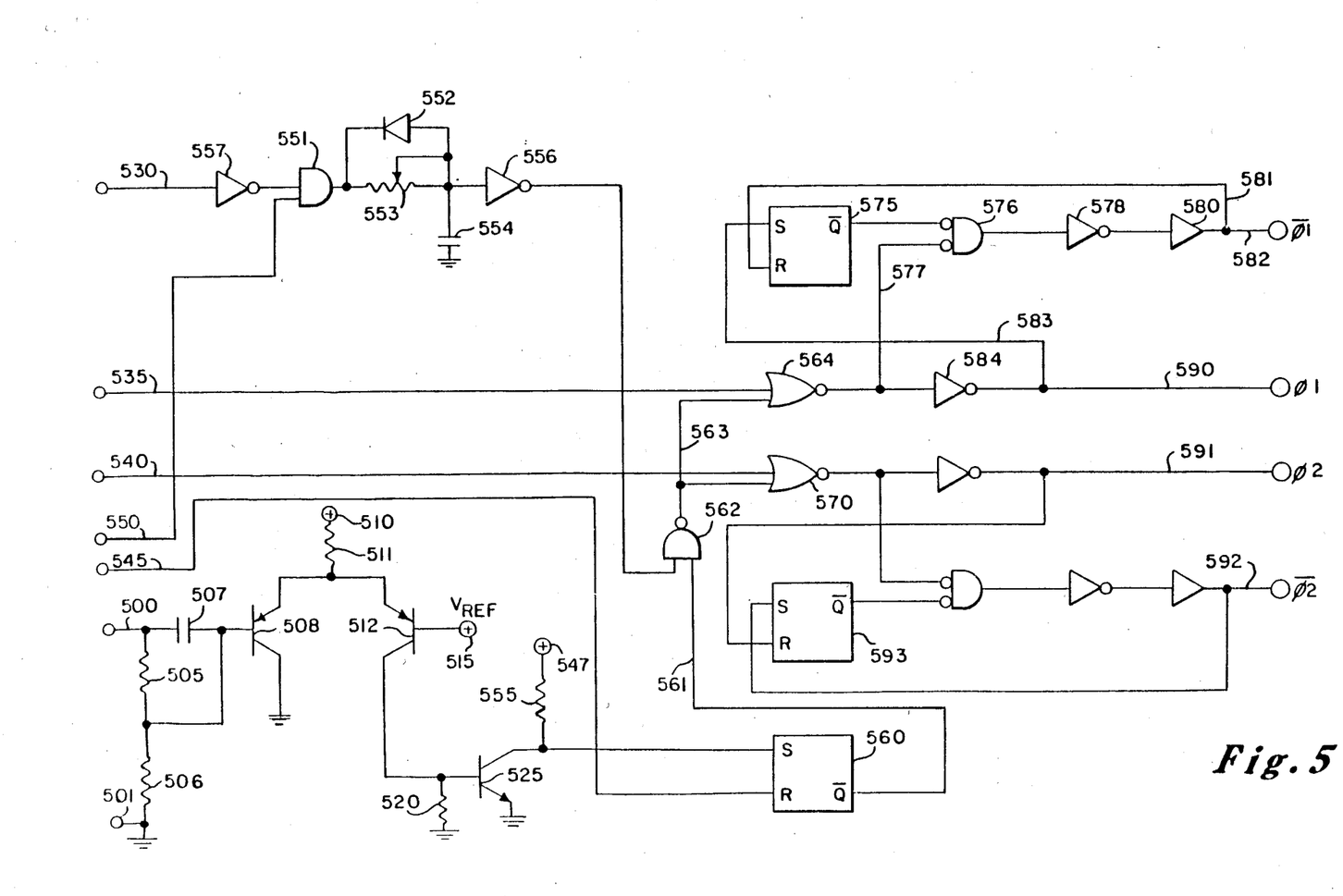

The detailed circuitry of the timing circuit is shown in FIGS. 4 and 5. FIG. 4 contains the detailed circuitry of divider 307, pulse generators 320 and 325, synchronizer 330, comparator 335, ramp generator 336, shift register 351 and the associated gate circuitry shown in FIG. 3. FIG. 5 shows in detail the current sense ano pulse width adjustment circuitry 390 and the output circuitry shown in block form in FIG. 3.

Referring to FIG. 4, the control circuitry receives a one megahertz clock signal on input terminal 4001, which signal is provided to the input of divider 4010 which as previously described, produces an output waveform with frequencies of 31.25 kilohertz on output 4011, 500 kilohertz on lead 4015, 250 kilohertz on lead 4022 and 125 kilohertz on output lead 4016. Output 4011 of divider 4010 is inverted by inverter 4012 and applied to the clock input of JK flip/flop 4025. Output 4015 of the divider 4010 is applied to the reset input of JK flip/flop 4025. Flip/flop 4025 is a well-known circuit device which produces a "high" signal on its Q output on the rising edge of a clock pulse if a "high" signal is provided to its J input ano a "low" signal is provided to its K input.

Figure 6:
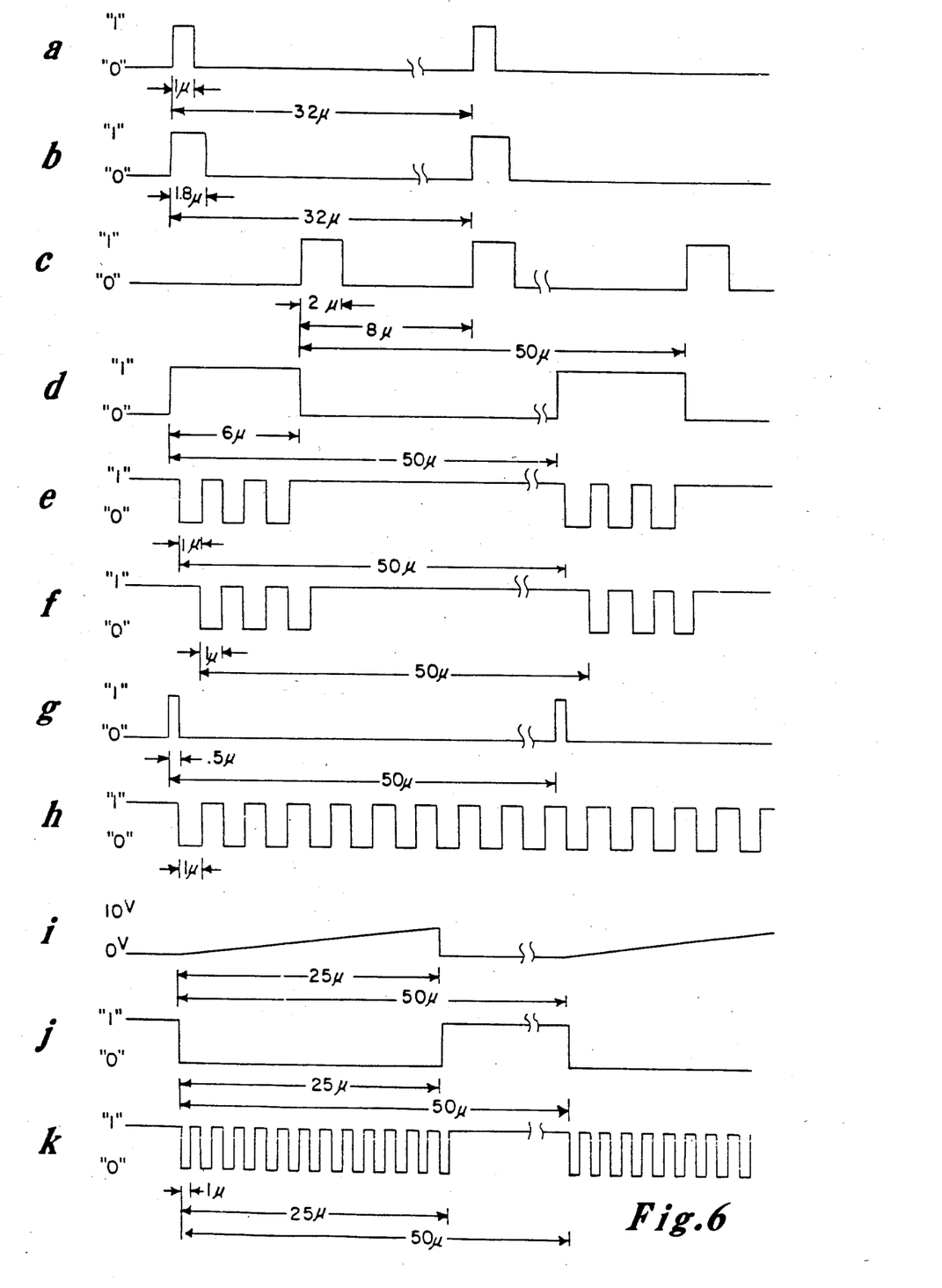
FIG. 6 shows selected electrical waveforms produced by the circuitry of FIGS. 4 and 5.

Assuming the control circuitry is conditioned to provide an output signal optimized for electrosurgical fulguration, a "high" signal appears on FULGURATION ENABLE lead 4000 and the "high" signal is provided to the J input of flip/flop 4025 by means of lead 4013. Therefore, in response to the signals provided to its clock and reset inputs, JK flip/flop 4025 provides on its Q output a signal which consists of a train of pulses 1 microsecond in duration with a 31.25 kilohertz repetition rate. In particular, flip/flop 4025 provides a "high" signal on its Q output on the rising edge of every clock pulse provided to its clock impulse from divider 4010. The flip/flop is reset to remove the "high" signal from the Q output in response to the 500 kilohertz signal provided to its reset input. The output of flip/flop 4025 is therefore the signal shown in FIG. 6, line A.

This signal is provided to the pulse-width determining circuitry consisting of the resistors 4031, 4036 and 4037, diode 4032, capacitor 4033 and comparator 4034. In particular, the high signal at the output of flip/flop 4025 charges capacitor 4033 via resistor 4031 and diode 4032. Resistor 4031 has a low value so capacitor 4033 charges quickly. The increasing voltage on capacitor 4033 is compared to a reference voltage source 4035 by comparator 4034. When the voltages are equal, comparator 4034 provides a "high" signal output and line 4040 is pulled "high" by resistor 4039 and voltage source 4038. When the output of flip/flop 4025 becomes low at the end of each one microsecond pulse, capacitor 4033 begins discharging through variable resistor 4036 and resistor 4037. Diode 4032 prevents capacitor 4033 from discharging through resistor 4031. Resistors 4036 and 4037 are of much higher value than the value of resistor 4031 and thus the discharge time of capacitor 4033 is much longer than its charging time. The pulse-width determining circuitry therefore acts as a pulse "stretcher" and the time at which the voltages at the inputs of comparator 4034 become equal is determined by the adjustment of resistor 4036. Similarly, the width of the pulses present at the comparator output 4040 is dependent on the adjustment of variable resistor 4036. In the illustrative embodiment, variable resistor 4036 is adjusted so that the width of the pulses produced on the output of comparator 4034 is approximately 1.85 microseconds as shown in line B of FIG. 6

The pulses on lead 4040 are connected to one input of ORgate 4041. Gate 4041 is an enabling gate and also receives signals from the dessication (coagulation) and cutting portions of the circuitry. As will be hereinafter described, when a "high" signal is present on any of the three inputs of gate 4041, "high" signals are produced on its output 4045 which enable the output shift register consisting of flip/flops 4066 and 4071 to produce clocking signals which operate the semiconductor switch circuits.

In particular, assuming the circuitry is in the fulguration mode, a "high" signal on FULGURATION ENABLE lead 4000 is applied to ANDgates 4063 and 4065 to enable them. The other inputs of ANDgates 4063 and 4065 are connected to the output of ORgate 4041 by means of lead 4045. Therefore, when a "high" signal appears at the output of comparator 4034 and lead 4040, ORgate 4041 produces a "high" signal on its output 4045 and enables ANDgates 4063 and 4065. These gates deliver a "high" pulse to the set inputs of JK flip/flops 4066 and 4071 at 31.25 kilohertz repetition rate. The signal on the output 4045 of ORgate 4041 is also applied to one input of NORgate 4061. Gate 4061 also receives a "low" input from the output of invertor 4060 which, in turn, receives the "high" signal on FULGURATION ENABLE lead 4000 at its input. Gate 4061 produces a "high" signal at its output only when both of its inputs are "low" and the "high" signal is applied via lead 4072 to the reset inputs of flip/flops 4066 and 4071. Thus flip/flops 4066 and 4071 receive set signals when the output of ORgate 4041 is high and reset signals when it is low. Flip/flops 4066 and 4071 therefore act as latches and produce an output signal which is similar to line B in FIG. 6 although slightly delayed in time. This operation occurs even though clock signals are provided from lead 4052 to the clock inputs of flip/flops 4066 and 4071, since, as is well-known in the art, the set and reset inputs override the clock inputs and signals present on the JK inputs. The signals appearing on the Q outputs of flip/flops 4066 and 4071 are provided to the output circuitry shown in FIG. 5 by means of leads 4140 and 4135 respectively.

Advantageously, according to the invention, during the fulguration mode of operation, output signals are produced on leads 4135 and 4140 by flip/flops 4066 and 4071 simultaneously. As previously described, during the fulguration mode of operation, the semiconductor switches are configured into a "totem pole" arrangement. Thus, the simultaneous signals produced by the outputs of flip/flops 4066 and 4071 control the semiconductor switches to turn "on" simultaneously, allowing the circuitry to produce the optimum fulguration waveform output.

Assuming now that the timing circuitry is configured in a dessication or coagulation mode of operation, a "low" signal appears on the FULGURATION ENABLE 4000 produced by the panel switches or other circuitry (not shown). In addition, a "high" signal appears on the COAG ENABLE lead 4002. This "high" signal is applied to the J input of flip/flop 4050, which constitutes the coagulation pulse generator designated as generator 325 in FIG. 3. Flip/flop 4050 receives a 20 kilohertz clock signal, via input terminal 4003, at its clock input. Since the K input of flip/flop 4050 is grounded, the flip/flop will provide a "high" signal on its Q output 4051 when a clock pulse is provided on input terminal 4003. Flip/flop 4050 also receives a reset signal, via lead 4053, from ANDgate 4023. Gate 4023, in turn, receives two input signals via leads 4016 and 4022. These signals are the 250 kilohertz signal and 125 kilohertz signal produced by divider 4010. Therefore, ANDgate 4023 produces a series of pulses of duration of 6 microseconds at a repetition rate of 125 kilohertz as shown in line C of FIG. 6. Since these pulses are provided to the reset input of flip/flop 4050, flip/flop 4050 is reset six microseconds after it is set by a clock input. Thus, flip/flop 4050 produces pulses with a duration of 6 microseconds at a 20 kilohertz repetition rate as shown in line D of FIG. 6. These pulses are provided via lead 4051 to ORgate 4041. In response to the pulse input, ORgate 4041 produces a "high" output on its output lead 4045. However, since a "low" signal now appears on FULGURATION ENABLE lead 4000, gates 4061, 4063 and 4065 are disabled and thus no signals are provided to the set and reset inputs of flip/flops 4066 and 4071. Instead, the "high" signal on lead 4045 at the output of ORgate 4041 is provided to, and enables, ANDgate 4062. With ANDgate 4062 enabled, the Q̄ output of flip/flop 4066 is coupled, via lead 4073, to the input of ANDgate 4062. The output of gate 4062 is connected, in turn, to the J input of flip/flop 4066.

When connected in this configuration flip/flop 4066 "toggles" and its outputs change state upon the rising edge of every clock pulse. This mode of operation continues as long as the high signal is present on the output of ORgate 4041. The Q output of flip/flop 4066 is provided, via lead 4070, to the J input of flip/flop 4071. The K input of flip/flop 4071 is connected to a "high" signal source. Thus, a "high" signal appearing at the Q output of flip/flop 4066 is shifted into flip/flop 4071 and appears as a "low" signal on its $\overline{Q}$ output on the rising edge of a clock pulse applied to the clock input of flip/flop 4071. Since both flip/flops 4066 and 4071 change states only on the rising edges of clock pulses applied via lead 4052, the $\overline{Q}$ output of flip/flop 4071 assumes the state of the $\overline{Q}$ output of flip/flop 4066 one clock pulse later. Since flip/flop 4066 is connected in a "toggle" mode, flip/flop 4071 also "toggles" but its outputs are exactly 180 degrees out-of-phase with the outputs of flip/flop 4066. The $\overline{Q}$ outputs of both flip/flops 4066 and 4071 are provided, via leads 4135 and 4140, to the output circuitry shown in FIG. 5. When ORgate 4041 is provided with the pulse output of flip/flop 4050 during the dessication mode of operation, the $\overline{Q}$ output of flip/flop 4066 appears as in line E of FIG. 6 and the $\overline{Q}$ output of flip/flop 4071 appears as line F of FIG. 6. As previously discussed, in the dessciation mode, these outputs operate opposite arms of the semiconductor switching bridge to provide a bipolar signal to the output transformers and filter circuitry which, in turn, provide an optimal dessciation waveform to the output electrodes.

Assume for purposes of illustration, that the timing circuitry is configured to provide a cutting waveform output. In the cutting configuration, as described previously, the circuitry has two modes: either pure cutting or cutting with hemostasis. When the circuitry is configured to provide a pure cut waveform, a "high" signal appears on CUT ENABLE lead 4004 and a "high" signal appears on PURE CUT lead 4005. The two "high" signals enable gate 4080 which, in turn, provides a "low" signal on its output lead 4081. This "low" signal is connected to the cathode of diode 4090 and causes diode 4090 to become forward-biased and disable the output of comparator 4088. In addition, forward-biased diode 4090 provides a "low" signal to K input of flip/flop 4094 to place it in the pure cutting mode as will be hereinafter described.

The "high" signal on CUT ENABLE lead 4004 is also provided to the J input of flip/flop 4082. Accordingly, on the rising edge of a clock pulse provided, via lead 4083, from 20 kilohertz clock input terminal 4003, flip/flop 4082 is set and provides a "high" signal on its Q output 4095 and a "low" signal on its $\overline{Q}$ output 4084. Flip/flops 4082 and 4094 together provide a synchronizer (designated as synchronizer 330 in FIG. 3) which is operable during the cutting with hemostasis mode. In particular, the "low" signal at the $\overline{Q}$ output of flip/flop 4082 is inverted by invertor 4085 and applied to capacitor 4087 via resistor 4086. After a short time (as determined by the R.C. charging constant) the voltage across capacitor 4087 becomes sufficient to reset flip/flop 4082. Thus, the output of flip/flop 4082 is a short-duration pulse which is synchronized to the rising edge of the 20 kilohertz clock signal provided on input terminal 4003 as shown in line G of FIG. 6. This short pulse is provided via lead 4095 to the set input of flip/flop 4094 which, in turn, sets the flip/flop.

In the pure cut mode, however, since the J input of flip/flop 4094 is grounded and the K input is also grounded via diode 4090, once set flip/flop 4094 produces a "low" signal on its $\overline{Q}$ output and a "high" signal on its Q output and remains in this state until reset. The "low" signal on the $\overline{Q}$ output of flip/flop 4094 is inverted by invertor 4046 and applied as a "high" signal, via lead 4047, to ORgate 4041. The continuous "high" signal at the input of ORgate 4041 enables the output shift register comprised of flip/flops 4066 and 4071 to cycle continuously, as previously described, providing a continuous output (shown in line H of FIG. 6) which results in a sine wave output being developed by the output circuitry and applied to the output electrodes. Operation of the circuitry continues in this manner until the "high" signal on the CUT ENABLE lead 4004 is changed to a "low" signal. A "low" signal on lead 4004 disables gate 4080 whch applies a "high" signal on its output 4081 to back-bias diode 4090. As will more fully be described later, back-biased diode 4090 releases the output 4091 of comparator 4088 and the K input terminal of flip/flop 4094. Comparator 4088 has a ramp signal applied to its positive input and a D.C. level applied to its negative input via the HEMO LEVEL input lead 4006. When the ramp voltage equals the voltage on lead 4006, comparator 4088 produces a "high" output allowing the K input of flip/flop 4094 to be pulled "high" by resistor 4098 and voltage source 4097. Therefore, on the next clock pulse provided via lead 4096 to flip/flop 4094 the flip/flop is reset causing a "high" signal to appear on its $\overline{Q}$ output. This "high" signal is inverted and applied as a "low" signal to ORgate 4041, disabling it and stopping the generation of a cutting output signal. Since a "low" signal on the CUT ENABLE lead is applied to the J input of flip/flop 4082, this flip/flop cannot be set again and the cutting output waveform ceases.

The timing circuitry may also be configured to operate in the cutting with hemostasis mode. In this configuration, a "high" signal appears on the CUT ENABLE lead 4004. A "low" signal appears on PURE CUT lead 4005. In addition, a D.C. level appears on HEMO LEVEL lead 4006 which D.C. level indicates the percentage of time during which the cutting waveform is to be present in the output signal. The "low" signal on PURE CUT lead 4005 disables gate 4080, in turn, back-biasing diode 4090, via lead 4081. Back-biased diode 4090 releases the output of comparator 4088, as will be hereinafter described. The "high" signal on CUT ENABLE lead 4004 is applied to the J input of flip/flop 4082. As previously described, flip/flop 4082 provides a synchronizing pulse on the rising edge of the 20 kilohertz clock signal (line G of FIG. 6) to the set input of flip/flop 4094. Since, the K input of flip/flop 4094 is no longer held "low" by forward-biased diode 4090, it is under control of comparator 4088 and voltage source 4097. Assume, for the moment, that the D.C. voltage on HEMO LEVEL lead 4006 is greater than the D.C. level on lead 4092, which level is applied to the positive input of comparator 4088. In this case, comparator 4088 produces a "low" signal on its output 4091 which is applied to the K input of flip/flop 4094. Therefore, as with the pure cutting mode, the set input of flip/flop 4094 receives a synchronizing pulse from flip/flop 4082. Flip/flop 4094 is set and produces a "low" signal on its $\overline{Q}$ output. This "low" signal, via inverter 4046, enables ORgate 4041 which, in turn, allows the shift register comprised of flip/flops 4066 and 4071 to oscillate in a free-running manner.

However, in addition, the "low" signal appearing at the output of flip/flop 4094 is applied via resistor 4105 to the base of transistor 4115. Transistor 4115 is normally held "off" by means of a voltage signal applied from flip/flop 4094. However, the "low" signal applied to resistor 4105 by flip/flop 4094 turns transistor 4115 "on". Turned-on transistor 4115, resistor 4110, resistor 4107 and diode 4106 form a constant-current source. Under control of transistor 4115, a constant level of current flows from source 4108, via variable resistor 4110, to charge capacitor 4093. The voltage across capacitor 4093 therefore increases linearly (as shown in line I of FIG. 6, assuming a 50% on/off ratio). The voltage across capacitor 4093 is provided, via lead 4092, to the positive input of comparator 4088. Eventually the voltage on lead 4092 will equal that on the HEMO LEVEL lead 4006. At this point the output of comparator 4088 becomes "high". When this occurs, source 4097 pulls the K input of flip/flop 4094 "high" via resistor 4098. Therefore, on the rising edge of the next clock pulse received at the clock input of flip/flop 4094 from leads 4052 and 4096, the $\overline{Q}$ output of flip/flop 4094 will become "high" and the Q output will become "low" as shown in line J of FIG. 6. A "high" signal on the $\overline{Q}$ output of flip/flop 4094 is inverted by invertor 4046 and disables ORgate 4041, thereby causing free-running oscillation of flip/flops 4066 and 4071 to cease.

In addition, when a synchronizing pulse is generated by flip/flop 4082, its $\overline{Q}$ output becomes "low". This "low" signal is applied via lead 4084 to one input of NANDgate 4125. The other input of NANDgate 4125 receives a "low" signal from the Q output of flip/flop 4094 via lead 4100. Gate 4125 therefore applies a "high" signal via lead 4120 and resistor 4118 to the base of transistor 4116 turning it "on". Turned-on transistor 4116 discharges capacitor 4093 thus resetting the ramp circuit. At the end of the set pulse generated by flip/flop 4082, the "low" signal is removed from the upper input of NANDgate 4125 by means of lead 4084 thereby turning "off" transistor 4116 and resetting the circuit to again charge capacitor 4093.

Therefore, it is clear that the period of free-running oscillation of flip/flops 4066 and 4071 is controlled by the D.C. level appearing on HEMO LEVEL lead 4006 and the relation of this voltage to the charging time of capacitor 4093. The output developed by the circuit is shown in line K of FIG. 6. With an appropriate adjustment of these components the output waveform can be suitably adjusted to produce an optimal cutting with hemostasis operation.

Referring now to FIG. 5, the current-limiting circuitry, pulse width adjust, and output circuitry is shown in detail. Specifically, the output circuitry is comprised of set-reset flip/flops 575 and 593 and associated circuitry. Since the output circuitry is duplicated to provide $\phi 1$ and $\phi 2$ outputs, only one set of output circuitry will be described in detail.

Specifically, output pulses appearing on the $\overline{Q}$ output of flip/flop 4066 are provided, via leads 4073, 4140 and 540; to the upper input of NORgate 570. Similarly, output pulses appearing on the $\overline{Q}$ output of flip/flop 4071 are provided, via leads 4135 and 535 to the upper input of NORgate 564. The other inputs of NORgates 564 and 570 are controlled by the current-limiting and pulse width adjustment circuitry as will be hereinafter described in detail. The signal appearing at the output of NORgate 564 is inverted by invertor 584 and appears at the $\phi 1$ output, terminal 590. As previously described, the pulses appearing at the $\phi 1$ and $\phi 2$ outputs are applied to the radio-frequency driver circuitry which, in turn, drives the semiconductor switches to produce output voltages.

Specifically, assuming NORgate 564 receives a "low" signal at its lower input, via lead 563, from the current-limiting and pulse width adjusting circuitry, it applies a "high" signal to invertor 584 which in turn applies a "low" signal to the $\phi 1$ output 590. This "low" signal as previously described turns "on" the radio-frequency driver circuitry. In addition, the "high" signal at the output of NORgate 564 is applied, via lead 557, to one input of NORgate 576 to disable it. In response, NORgate 576 places a "low" signal on its output which is applied to the input of invertor 578 which, in turn, places a "high" signal on its output. The "high" signal at the output of invertor 578, in turn, is applied to the $\overline{\phi 1}$ output by buffer gate 580. At this time, the "high" signal at the $\overline{\phi 1}$ output is also applied to the set input of set-reset flip/flop 575. This high signal sets the flip/flop to produce a "low" signal at its $\overline{Q}$ output, which signal is applied to the upper input of gate 576. Gate 576, however, is still held in the "off" state by the "high" signal at its lower input.

At the end of the output pulse produced by flip/flop 4071, the signal on the $\overline{Q}$ output of flip/flop 4071 becomes "high". This signal, in turn, disables NORgate 564, causing it to place a "low" signal on its output. This "low" signal is inverted by invertor 584 and appears as a "high" signal on the $\phi 1$ output which, in turn, turns "off" the radio-frequency drivers, as previously described. The "low" signal on the output of NORgate 564 is also applied to the lower input of gate 576 thereby enabling it causing it to produce a "high" signal on its output which signal is inverted by invertor 578 and passes through buffer amplifier 580 as a "low" signal to the $\overline{\phi 1}$ output. As previously described, this signal is used to "dump" the flux in the driver transformer of the associated radio-frequency driver circuitry.

The "low" signal on the output $\overline{\phi 1}$ is also applied to the set input of set-reset flip/flop 575, setting the flip-flop which, in turn, produces a "high" signal on its output $\overline{Q}$ which signal disables gate 576. Disabled gate 576 produces a "low" signal output which "low" signal is inverted by invertor 578 and applied to buffer amplifier 580. Amplifier 580 produces a "high" signal on the $\overline{\phi 1}$ output of terminal 582. The signal on the $\overline{\phi 1}$ is therefore "low" only for a short period of time which is equal to the cumulative propagation delay of set-reset flip/flop 575 and gates 576, 578 and 580. This cumulative delay totals approximately 200 nanoseconds. The 200 nanosecond pulse produced on the $\overline{\phi 1}$ output, as described above is used to "dump" the flux from the transformer of the associated radio-frequency driver circuit to insure a quick turn-off of the semiconductor switch circuits.

The $\phi 2$ and $\overline{\phi 2}$ outputs associated with the output terminals 591 and 592 operate in an exactly similar way driven by the output signal provided by NORgate 570 and flip/flop 593.

In order to prevent damage to the semiconductor switches NORgates 564 and 570 are controlled by the current-limiting and pulse width adjustment circuit consisting of transistors 508, 512 and 525 and set-reset flip/flop 560 and gate 551 and its associated circuitry. Specifically, as the current flowing through the semiconductor switches increases set-reset flip/flop 560 becomes set during the output signal pulse produced by the control circuitry and disables gates 564 and 570 turning "off" the output signal before "turn off" would normally occur. In particular, as previously described, as the current through the semiconductor switches increases, the potential drop across the current sense input terminals 500 and 501 increases. This potential is impressed across the resistive divider consisting of resistors 505 and 506. An increasing potential at the junction of resistors 505 and 506 is applied to the base of transistor 508. Capacitor 507 helps to speed up the operation of transistor 508. Transistor 508 together with transistor 512 comprise a differential amplifier. According to well-known principles of differential amplifiers, as transistor 508 turns "off" in response to the increasing potential at the junction of resistors 505 and 506 transistor 512 becomes more "turned on". Specifically, as transistor 508 turns "off", less current is drawn therethrough and the current running through resistor 511 from voltage source 510 decreases. Thus, the potential at the emitter of transistor 508 increases. Since the base of transistor 512 is connected to the voltage reference source 515 transistor 512 tends to be "turned on" and increases its current flow. An increased current flow from the collector of transistor 512 is applied to resistor 520 and the base of transistor 525 tending to turn it "on". As transistor 525 turns "on" the current through it increases thereby increasing the voltage drop from supply 547 across resistor 555. Therefore, with increasing current the signal applied to the set input of set-reset flip/flop 560 decreases.

At some point flip/flop 560 is set and its $\overline{Q}$ output becomes "low". The "low" signal is applied to one input of NANDgate 562, which, in turn, applies a "high" signal to gates 564 and 570, disabling them. Thus, as the current through the semiconductor switches increases gate 564 and 570 are turned off earlier and earlier during the "on" cycle, reducing the effective pulse width of the control circuit output signal and the current flowing through the semiconductor switches. At the end of the pulse, a "low" signal provided, via lead 545, from the output of ORgate 4041 to the reset input of set-reset flip/flop 560 resets the flip/flop for another cycle.

The pulse width adjustment, circuit consisting of gate 551, diode 552, resistor 553, capacitor 554 and Schmidt trigger circuit 556, is used to adjust the width of the pulses produced by the output circuitry as previously described so that successive pulses do not overlap. This circuitry is operative only during the cutting and coagulation modes when the bridge switching circuit is active. Specifically, during the cutting and coagulation modes, the FULGURATION ENABLE lead 4000 (FIG. 4) has a "low" signal thereon. This "low" signal is transmitted via leads 4130 and 530 to inverter 557 which, in turn, applies a "high" signal to the upper input of ANDgate 551. The lower input of gate 551 receives a 1 megahertz clock signal from leads 4150 and 550. Thus gate 551 produces a "high" output during the "high" portion of the clock signal. The "high" output of gate 551 charges capacitor 554 via variable resistor 553. When the voltage across capacitor 554 reaches the threshold voltage of Schmidt trigger circuit 556, circuit 556 applies a "low" signal to NANDgate 562 The "low" signal on its inputs causes gate 562 to apply a "high" signal to gates 564 and 570 disabling them. Therefore, the width of the pulses produced by gates 564 and 570 can be controlled by adjusting variable resistor 553. This resistor is adjusted so that succesive pulses do not overlap.

Although specific circuitry is shown on the illustrative embodiment there will be many variations of the illustrative embodiment which will be immediately apparent to those skilled in the art and which embody the spirit of the invention.

What is claimed:

1. In a electrosurgical generator for performing an electrosurgical operation which requires a periodically interrupted waveform, said generator having output circuitry for connection to a patient and means controllable by an operating surgeon for selecting said electrosurgical operation, the improvement comprising:

power amplifier means responsive to said selecting means for selectively generating a periodically interrupted rectangular waveform with a fundamental frequency, duty cycle, current and voltage suitable for performing said electrosurgical operation; and filter means responsive to said rectangular waveform for converting said rectangular waveform to an output waveform suitable for performing said electrosurgical operation and for providing said ouput waveform to said output circuitry, said filter acting as a voltage doubler and producing an output wave form having a peak voltage equal to twice the peak voltage of said rectangular waveform.

2. An electrosurgical generator according to claim 1 wherein said power amplifier means is a class D amplifier.

3. An electrosurgical generator according to claim 2 wherein said filter means is a bandpass filter.

4. An electrosurgical generator for performing electrosurgical operation comprising, a D.C. power source;
output electrodes for connection to a patient;
a plurality of switches connected in a bridge configuration having four arms, one of said switches being located in each arm;
a bandpass filter having an input and having an output connected to said output electrodes;
a transformer having a primary winding and having a secondary winding connected to said input of said filter; and
means for generating timing signals to alternately operate pairs of said switches in diagonally-opposite arms to connect said primary winding to said power source.

5. An electrosurgical generator according to claim 4 wherein said bandpass filter is a passive LC network.

6. An electrosurgical generator according to claim 5 wherein said electrodes are bipolar and said bandpass filter is a series LC filter.

7. An electrosurgical generator according to claim 5 wherein said electrodes are monopolar and said bandpass filter comprises a series LC filter connected in series with a parallel LC filter.

8. An electrosurgical generator for performing electrosurgical operation comprising, a D.C. power source;
bipolar output electrodes for connection to a patient;
monopolar output electrodes for connection to patient;
a plurality of switches connected in a bridge configuration having four arms, one of said switches being located in each arm;
a first bandpass filter having an input and having an output connected to said bipolar output electrodes;

a second bandpass filter having an input and having an output connected to said monopolar electrodes;

a first transformer having a primary winding and a secondary winding connected to said input of said first filter;

a second transformer having a primary winding and a secondary winding connected to said input of said second filter; and means for selectively connecting said first transformer winding and said second transformer winding to said switch bridge; and means for generating timing signals to alternately operate pairs of said switches in diagonally-opposite arms to connect said first primary winding and said second primary winding to said power source.

9. An electrosurgical generator according to claim 8 wherein said first and said second bandpass filters are passive LC networks.

10. An electrosurgical generator according to claim 9 wherein said first bandpass filter is a series LC filter.

11. An electrosurgical generator according to claim 9 wherein said second bandpass filter, comprises a series LC filter connected in series with a parallel LC filter.

* * * * *